(12) United States Patent
Greco et al.

(10) Patent No.: US 6,710,061 B2
(45) Date of Patent: Mar. 23, 2004

(54) AMINOPYRROLIDINE SULFONAMIDES AS SERINE PROTEASE INHIBITORS

(75) Inventors: Michael N. Greco, Lansdale, PA (US); Bruce E. Maryanoff, Forest Grove, PA (US); Michael J. Hawkins, Ambler, PA (US); Robert E. Boyd, Horsham, PA (US)

(73) Assignee: Ortho-McNeil Pharamceutical, Inc., Raritan, NJ (US)

( * ) Notice: Subject to any disclaimer, the term of this patent is extended or adjusted under 35 U.S.C. 154(b) by 137 days.

(21) Appl. No.: 10/303,230

(22) Filed: Nov. 25, 2002

(65) Prior Publication Data

US 2003/0166681 A1 Sep. 4, 2003

Related U.S. Application Data

(63) Continuation-in-part of application No. 10/090,872, filed on Mar. 5, 2002, now Pat. No. 6,538,017.
(60) Provisional application No. 60/274,845, filed on Mar. 9, 2001.

(51) Int. Cl.[7] ................... A61K 31/445; C07D 211/56; A61P 43/00
(52) U.S. Cl. ....................................... 514/329; 546/224
(58) Field of Search ........................... 546/224; 514/329

(56) References Cited

U.S. PATENT DOCUMENTS

| | | | |
|---|---|---|---|
| 5,607,937 A | 3/1997 | Stuerzebecher et al. | |
| 5,612,353 A | 3/1997 | Ewing et al. | |
| 5,747,535 A | 5/1998 | Oh et al. | |
| 5,770,600 A | 6/1998 | Abelman et al. | |
| 5,843,906 A | * 12/1998 | Chandrakumar et al. | ..... 514/19 |
| 5,869,501 A | 2/1999 | Hirayama et al. | |
| 5,935,959 A | 8/1999 | Inoue et al. | |

FOREIGN PATENT DOCUMENTS

| | | |
|---|---|---|
| EP | 0 203 743 A1 | 12/1986 |
| EP | 0 299 493 A2 | 1/1989 |
| EP | 0 623 A1 | 11/1994 |
| EP | 0623595 A1 | 11/1994 |
| EP | 0 739 886 A2 | 10/1996 |
| WO | WO 96/05189 A1 | 2/1996 |
| WO | WO 96/1022 A1 | 4/1996 |
| WO | WO 96/16940 A1 | 6/1996 |
| WO | WO 96/40679 A1 | 12/1996 |
| WO | WO 96/40737 A1 | 12/1996 |
| WO | WO 97/19919 A1 | 6/1997 |
| WO | WO 97/40023 A1 | 10/1997 |
| WO | WO 98/05336 A1 | 2/1998 |
| WO | WO 98/54164 A1 | 12/1998 |
| WO | WO 98 57934 | 12/1998 |

OTHER PUBLICATIONS

Kaiser, Brigitte, Thrombin and Factor Xa Inhibitors, *Drugs of the Future*, 1998, 23(4), 423–436.
Kunitada, S., et al., Factor Xa Inhibitors, *Current Pharmaceutical Design*, 1996, 2, 531–542.
*Drugs of the Future* 1999, 24(7), 771–787.
Evmolieff, J., et al, Proteolytic Activation of Recombinant Pro–memapsin 2 (Pro–□–secretase) Studied with New Fluorogenic Substrates, *Biochemistry*, 2000, 39, 12450–12456.
*Syn. Comm.* 1992, 22(19) 2357.
*Syn. Comm.* 1993, 23(10), 1443.

\* cited by examiner

*Primary Examiner*—Joseph K. McKane
*Assistant Examiner*—Andrea D. Small
(74) *Attorney, Agent, or Firm*—Hal B. Woodrow

(57) ABSTRACT

The present invention is directed to compounds useful as selective serine protease or dual-serine protease inhibitors, compositions thereof and methods for treating serine protease or dual-serine protease mediated disorders.

23 Claims, No Drawings

AMINOPYRROLIDINE SULFONAMIDES AS SERINE PROTEASE INHIBITORS

CROSS REFERENCE TO RELATED APPLICATIONS

This application is a continuation-in-part of U.S. application Ser. No. 10/090,872 filed Mar. 5, 2002 now U.S. Pat. No. 6,538,017, and claims benefit of provisional application Serial No. 60/274,845, filed Mar. 9, 2001, which are hereby incorporated by reference.

FIELD OF THE INVENTION

The present invention relates to certain novel compounds, methods for preparing the compounds, compositions, intermediates and derivatives thereof and for treating serine protease mediated disorders. More particularly, the aminopyrrolidine sulfonamide compounds of the present invention are selective serine protease or dual-serine protease inhibitors of Factor Xa and tryptase useful for treating serine protease or dual-serine protease mediated disorders.

BACKGROUND OF THE INVENTION

Thrombotic disorders are a major cause of mortality in industrialized countries (Kaiser, Brigitte, Thrombin and Factor Xa Inhibitors, *Drugs of the Future*, 1998, 23(4), 423–436). Thrombin has been a target for the development of anticoagulation agents because it occupies a central position in the coagulation cascade (Kunitada, S., et al., Factor Xa Inhibitors, *Current Pharmaceutical Design*, 1996, 2, 531–542). Since Factor Xa (FXa) is responsible for the formation of thrombin, a FXa inhibitor has become an alternative strategy to selectively prevent thrombin production and clot formation.

Like thrombin, FXa is a member of the serine protease superfamily. In the blood coagulation cascade, FXa links the intrinsic and extrinsic activation pathways for the production of thrombin. In the intrinsic pathway, Factor IXa converts Factor X to FXa in the presence of Factor VIIIa, $Ca^{2+}$ and phospholipid. In the extrinsic pathway, Factor VIIa converts Factor X to FXa in the presence of tissue factor. Once formed, FXa binds to Factor Va on phospholipid surfaces in the presence of $Ca^{2+}$ ions to form the prothrombinase complex, which is responsible for converting prothrombin to thrombin. Thrombin in turn converts fibrinogen to fibrin, which ultimately results in the production of a fibrin clot.

Potential advantages for FXa inhibitors as anticoagulants stem from the inhibition of thrombin formation rather than inhibition of its catalytic activity. For example, it is expected that thrombin-induced platelet activation could still occur under FXa inhibition, thus minimizing bleeding risk. The thrombin/thrombomodulin complex downregulates thrombin production, thus functioning as an endogenous anticoagulant. It has been postulated that FXa inhibition would supply sufficient thrombin for this interaction, which might minimize the "thrombotic rebound" effect observed in the clinical use of direct thrombin inhibitors.

A comprehensive review of FXa inhibitors has recently appeared (*Drugs of the Future* 1999, 24(7), 771–787).

PCT application WO 96/10022 to Faull, et. al., describes sulfonylpiperazine-derived FXa inhibitors of the formula:

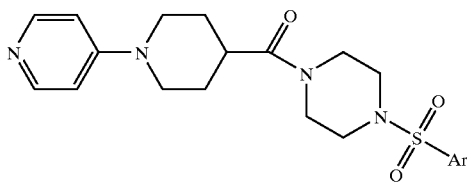

PCT application WO 98/54164 to Tawada, et. al., describes sulfonylpiperazine-derived FXa inhibitors of the formula:

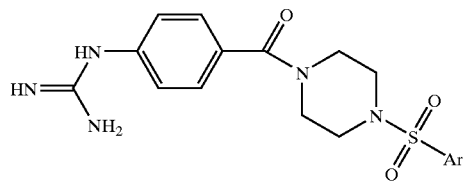

Accordingly, it is an object of the invention to provide aminopyrrolidine sulfonamide-derived compounds that are serine protease inhibitors; in particular, selective serine protease or dual-serine protease inhibitors of Factor Xa and tryptase. It is another object of the invention to provide a process for preparing aminopyrrolidine sulfonamide compounds, compositions, intermediates and derivatives thereof. It is a further object of the invention to provide methods for treating serine protease or dual-serine protease mediated disorders.

SUMMARY OF THE INVENTION

This invention is directed to aminopyrrolidine sulfonamide compounds selected from the group consisting of Formula (I) and Formula (II):

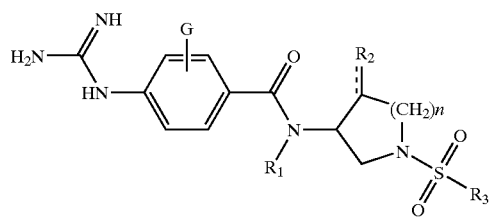

Formula (I)

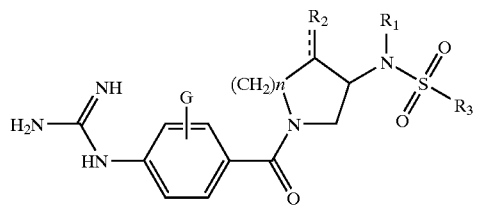

Formula (II)

wherein
$R_1$ is selected from the group consisting of hydrogen, $C_{1-8}$alkyl, $C_{3-7}$cycloalkyl, aryl, aryl($C_{1-8}$)alkyl, aryl($C_{2-8}$)alkenyl, heteroaryl($C_{1-8}$)alkyl, heteroaryl($C_{2-8}$) alkenyl and $R_4C(O)CH_2—$; wherein aryl and heteroaryl are optionally substituted with one to two substituents independently selected from $R_4$;
$R_2$ is selected from the group consisting of hydrogen, hydroxy, $C_{1-8}$alkoxy, aryloxy and aryl($C_{1-8}$)alkoxy; with the proviso that $R_2$ is bonded to the heterocyclyl ring by a single bond; alternatively, $R_2$ is oxo; with the proviso that $R_2$ is bonded to the heterocyclyl ring by a double bond;

$R_3$ is selected from the group consisting of aryl, aryl($C_{1-8}$)alkyl, aryl($C_{2-8}$)alkenyl, heteroaryl($C_{1-8}$)alkyl, heteroaryl($C_{2-8}$)alkenyl; wherein aryl and heteroaryl are optionally substituted with one to three substituents independently selected from the group consisting of halogen, $C_{1-8}$alkyl, $C_{1-8}$alkoxy, amino, ($C_{1-4}$alkyl)amino, di($C_{1-4}$alkyl)amino, trihalo($C_{1-8}$)alkyl and trihalo($C_{1-8}$)alkoxy;

$R_4$ is selected from the group consisting of hydroxy, amino, $C_{1-8}$alkyl, ($C_{1-4}$alkyl)amino, di($C_{1-4}$alkyl)amino, $C_{1-8}$alkoxy, carboxy, carboxy($C_{1-8}$)alkyl, carboxy($C_{1-8}$)alkoxy, (carboxy)amino, (carboxy($C_{1-4}$)alkyl)amino, (carboxyaryl)amino, (carboxyaryl($C_{1-4}$)alkyl)amino, (carboxy($C_{1-4}$)alkylaryl)amino, aryloxy, aryl($C_{1-8}$)alkoxy, (aryl)amino, (aryl($C_{1-4}$)alkyl)amino, ($C_{1-4}$alkylaryl)amino, (arylcarboxy)amino, di(aryl)amino, di(aryl($C_{1-4}$)alkyl)amino, $C_{1-8}$alkoxycarbonyl, $C_{1-8}$alkoxycarbonyl($C_{1-8}$)alkoxy, aminocarbonyl, ($C_{1-8}$alkyl)aminocarbonyl, (carboxy($C_{1-8}$)alkyl)aminocarbonyl, ($C_{1-8}$alkoxycarbonyl($C_{1-8}$)alkyl)aminocarbonyl and guanidino; and, G is selected from the group consisting of hydrogen, halogen, hydroxy, $C_{1-4}$alkyl, $C_{1-8}$alkoxy, aryl, aryloxy, aryl($C_{1-8}$)alkyl, aryl($C_{1-8}$)alkoxy, amino, carboxy, alkylaminocarbonyl, alkylcarbonylamino, trihalo($C_{1-8}$)alkyl and trihalo($C_{1-8}$)alkoxy;

n is 1 or 2;

and pharmaceutically acceptable salts thereof.

The aminopyrrolidine sulfonamide compounds of the present invention are selective serine protease or dual-serine protease inhibitors useful for treating serine protease mediated disorders. An embodiment of the invention includes compounds that are selective or dual-inhibitors of Factor Xa and tryptase.

The present invention includes a method for preparing instant compounds, compositions, intermediates and derivatives thereof and a method for treating selective serine protease or dual-serine protease mediated disorders.

DETAILED DESCRIPTION OF THE INVENTION

An embodiment of the instant compounds are those wherein, preferably, $R_1$ is selected from the group consisting of hydrogen, aryl($C_{1-8}$)alkyl and heteroaryl($C_{1-8}$)alkyl, wherein aryl, heteroaryl and the aryl and heteroaryl portion of arylalkyl and heteroarylalkyl are optionally substituted with a substituent selected from $R_4$. More preferably, $R_1$ is selected from the group consisting of hydrogen, benzyl, phenethyl, phenylpropyl and benzofurylmethyl, wherein phenyl, the phenyl portion of benzyl and the benzofuryl portion of benzofurylmethyl are optionally substituted with a substituent selected from $R_4$. Most preferably, $R_1$ is selected from the group consisting of hydrogen, benzyl, phenylpropyl and benzofurylmethyl, wherein phenyl, the phenyl portion of benzyl and the benzofuryl portion of benzofurylmethyl are optionally substituted with a substituent selected from $R_4$.

An embodiment of the instant compounds also include those wherein, preferably, $R_2$ is hydrogen.

An embodiment of the instant compounds further includes those wherein, preferably, $R_3$ is aryl($C_{2-8}$)alkenyl, wherein aryl is optionally substituted with one to three substituents independently selected from halogen. More preferably, $R_3$ is independently selected from the group consisting of phenethenylene and phenylpropenylene, wherein phenyl is optionally substituted with one to three substituents independently selected from the group consisting of chlorine and fluorine. Most preferably, $R_3$ is phenethenylene, wherein phenyl is substituted with one to three substituents selected from chlorine.

Embodiments of the instant compounds include those wherein, preferably, $R_4$ is selected from the group consisting of hydroxy, di($C_{1-4}$alkyl)amino, $C_{1-8}$alkoxy, carboxy, carboxy($C_{1-8}$)alkoxy, aryl($C_{1-8}$)alkoxy, $C_{1-8}$alkoxycarbonyl, $C_{1-8}$alkoxycarbonyl($C_{1-8}$)alkoxy, aminocarbonyl, ($C_{1-8}$alkyl)aminocarbonyl, (carboxy($C_{1-8}$)alkyl)aminocarbonyl and $C_{1-8}$alkoxycarbonyl($C_{1-8}$)alkyl)aminocarbonyl.

More preferably, $R_4$ is selected from the group consisting of hydroxy, carboxy, carboxy($C_{1-8}$)alkoxy, $C_{1-8}$alkoxycarbonyl, $C_{1-8}$alkoxycarbonyl($C_{1-8}$)alkoxy, aminocarbonyl, (carboxy($C_{1-8}$)alkyl)aminocarbonyl and $C_{1-8}$alkoxycarbonyl($C_{1-8}$)alkyl)aminocarbonyl.

Most preferably, $R_4$ is selected from the group consisting of hydroxy, carboxy, carboxymethoxy, methoxycarbonyl, aminocarbonyl, (carboxymethylene)aminocarbonyl and methoxycarbonylmethlene)aminocarbonyl.

Embodiments of the instant compounds also include those wherein, preferably, G is selected from the group consisting of hydrogen, halogen, hydroxy, $C_{1-4}$alkyl, $C_{1-8}$alkoxy, aryl, aryloxy, aryl($C_{1-8}$)alkyl, aryl($C_{1-8}$)alkoxy, amino and trihalo($C_{1-8}$)alkyl. More preferably, G is hydrogen.

The compounds of the present invention are exemplified by a compound of the formula:

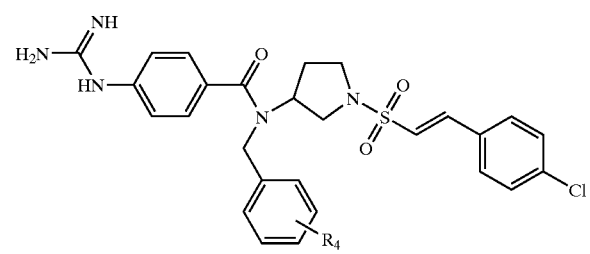

wherein $R_4$ is selected from:

| Cpd | $R_4$ |
|---|---|
| 2 | 4-OH; |
| 3 | 4-$CO_2CH_3$; |
| 4 | 3-$CO_2CH_3$; |
| 5 | 4-$CO_2H$; |
| 6 | 3-$CO_2H$; |
| 7 | 3-OH; |
| 8 | 3-$OCH_2CO_2CH_3$; |
| 9 | 4-$CONH_2$; |
| 10 | 4-$CONHCH_2CO_2CH_3$; |
| 11 | 3-$OCH_2CO_2H$; |
| 12 | 4-$CONHCH_2CO_2H$; |
| 13 | 3-$CONHCH_2CO_2CH_3$; |
| 14 | 3-$CONHCH_2CO_2H$; |
| 15 | 3-$CONH_2$; |
| 24 | 4-NHC(=NH)$NH_2$; or, |
| 25 | 3-$CO_2CH_3$-4-OH; | and pharmaceutically acceptable salts thereof.

The compounds of the present invention are also exemplified by a compound of the formula:

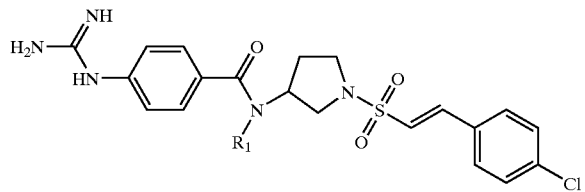

wherein $R_1$ is:

| Cpd | $R_1$ |
|---|---|
| 1 | $PhCH_2$; |
| 26 | H; or, |
| 27 | 2-benzofuryl$CH_2$ | and pharmaceutically acceptable salts thereof.

The compounds of the present invention are further exemplified by a compound of the formula:

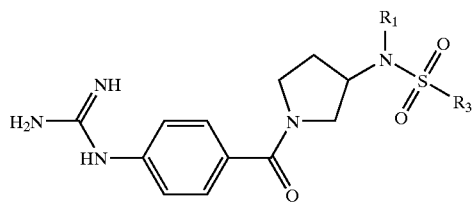

wherein $R_1$ and $R_3$ are dependently selected from:

| Cpd | $R_1$ | $R_3$ |
|---|---|---|
| 16 | $PhCH_2$ | 4-ClPh(CH)$_2$; |
| 17 | 4-(PhCH$_2$O)PhCH$_2$ | 4-ClPh(CH)$_2$; |
| 18 | 4-[(CH$_3$)$_2$N]PhCH$_2$ | 4-ClPh(CH)$_2$; |
| 19 | 4-(CH$_3$O)PhCH$_2$ | 4-ClPh(CH)$_2$; |
| 20 | Ph(CH$_2$)$_3$ | 4-ClPh(CH)$_2$; |
| 21 | 4-CO$_2$HPhCH$_2$ | 4-ClPh(CH)$_2$; |
| 22 | 4-[CH$_3$OC(O)]PhCH$_2$ | 4-ClPh(CH)$_2$; or, |
| 23 | PhCH$_2$ | 7-CH$_3$O-2-naphthalenyl; | and pharmaceutically acceptable salts thereof.

The compounds of the present invention may also be present in the form of a pharmaceutically acceptable salt. The pharmaceutically acceptable salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

Resonance forms for compounds of the present invention include those forms where an unsaturated bond may resonate between 2 or more atoms. For example, a guanidino group includes resonance forms represented by the formulae: —NH—C(=NH)—NH$_2$ or —N=C(NH$_2$)—NH$_2$. It is to be understood that all such resonance forms are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "alkyl" refers to straight and branched-chain alkyl radical groups; similarly, alkenyl and alkynyl radicals include straight and branched chains having 2 to 8 carbon atoms or any number within this range; wherein one or two double or triple bonds are formed in the chain between adjacent members. The term "alkoxy" refers to O-alkyl groups where alkyl is as defined supra. The term "cycloalkyl" refers to a cyclic alkyl ring of five to seven carbon atom members. Examples of such cyclic alkyl rings include pentyl, hexyl or heptyl.

The term "heterocyclyl" refers to a saturated or partially unsaturated ring having five members of which at least one member is a N, O or S atom and which optionally contains one additional O atom or one, two or three additional N atoms, a saturated or partially unsaturated ring having six members of which one, two or three members are a N atom, a saturated or partially unsaturated bicyclic ring having nine members of which at least one member is a N, O or S atom and which optionally contains one, two or three additional N atoms or a saturated or partially unsaturated bicyclic ring having ten members of which one, two or three members are a N atom. Examples include, and are not limited to, pyrrolinyl, pyrrolidinyl, 1,3-dioxolanyl, imidazolinyl, imidazolidinyl, pyrazolinyl, pyrazolidinyl, piperidinyl, morpholinyl or piperazinyl.

The term "aryl" refers to a single aromatic ring of six carbon members or a bicyclic aromatic ring of ten carbon members. Examples of such aryl rings include phenyl and naphthyl.

The term "heteroaryl" refers to an aromatic monocyclic ring system containing five members of which at least one member is a N, O or S atom and which optionally contains one, two or three additional N atoms; an aromatic monocyclic ring having six members of which one, two or three members are a N atom; an aromatic bicyclic ring having nine members of which at least one member is a N, O or S atom and which optionally contains one, two or three additional N atoms; or, an aromatic bicyclic ring having ten members of which one, two or three members are a N atom. Examples include, and are not limited to, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, indolyl, indazolyl, benzo[b]furyl, benzo[b]thienyl, quinolinyl, isoquinolinyl or quinazolinyl.

The term "carbonyl" as used herein refers to the organic radical linking group: R—C(O)—R having a single carbon atom; the term "carboxy" as used herein refers to the organic radical terminal group: R—C(O)OH.

The term "halogen" or "halo" shall include iodine, bromine, chlorine and fluorine.

Whenever the term "alkyl" or "aryl" or either of their prefix roots appear in a name of a substituent (e.g., aryl ($C_1$–$C_4$)alkyl, di($C_1$–$C_4$ alkyl)amino) it shall be interpreted as including those limitations given above for "alkyl" and "aryl." Designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

The term "aryl($C_{1-8}$)alkyl" or the coextensive term "arylalkyl" means an alkyl group substituted at the terminal carbon with an aryl group (e.g., benzyl, phenethyl). Similarly, the term "heteroaryl($C_{1-8}$)alkyl" or the coextensive term "heteroarylalkyl" means an alkyl group substituted at the terminal carbon with a heteroaryl group. The term "aryl($C_{1-8}$)alkoxy" or the coextensive term "arylalkoxy" indicates an alkoxy group substituted at the terminal carbon with an aryl group (e.g., benzyloxy).

When a particular group is "substituted" (e.g., Phe, aryl, heteroaryl), that group may have one or more substituents, preferably from one to five substituents, more preferably from one to three substituents, most preferably from one to two substituents, independently selected from the list of substituents.

Under standard nomenclature rules used throughout this disclosure, the terminal portion of the designated side chain is described first followed by the adjacent functionality toward the point of attachment. Thus, for example, a "phenyl$C_{1-6}$alkylamido$C_{1-6}$alkyl" substituent refers to a group of the formula:

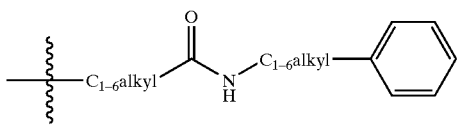

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The aminopyrrolidine sulfonamide-derived compounds of the present invention are selective serine protease or dual-serine protease inhibitors; in particular, selective or dual-inhibitors of Factor Xa and tryptase useful for treating selective serine protease or dual-serine protease mediated disorders.

Embodiments of the method of the present invention include a method for treating or ameliorating a serine protease or dual-serine protease mediated disorder in a subject in need thereof comprising administering to the subject a therapeutically effective amount of an instant compound or pharmaceutical composition thereof. The therapeutically effective amount of the compounds selected from the group consisting of Formula (I) and Formula (II) exemplified in such a method is from about 0.001 mg/kg/day to about 300 mg/kg/day.

Embodiments of the present invention include the use of a compound selected from the group consisting of Formula (I) and Formula (II) for the preparation of a medicament for treating or ameliorating a serine protease or dual-serine protease mediated disorder in a subject in need thereof.

In accordance with the methods of the present invention, an individual compound of the present invention or a pharmaceutical composition thereof can be administered separately at different times during the course of therapy or concurrently in divided or single combination forms. The instant invention is therefore to be understood as embracing all such regimes of simultaneous or alternating treatment and the term "administering" is to be interpreted accordingly.

Embodiments of the present method include a compound or pharmaceutical composition thereof advantageously co-administered in combination with other agents for treating or ameliorating a serine protease or dual-serine protease mediated disorder. For example, in the treatment of thrombosis, a compound selected from the group consisting of Formula (I) and Formula (II) or pharmaceutical composition thereof may be used in combination with other agents.

The combination product comprises co-administration of a compound selected from the group consisting of Formula (I) and Formula (II) or pharmaceutical composition thereof and an additional agent for treating or ameliorating a serine protease or dual-serine protease mediated disorder, the sequential administration of a compound selected from the group consisting of Formula (I) and Formula (II) or pharmaceutical composition thereof and an additional agent for treating or ameliorating a serine protease or dual-serine protease mediated disorder, administration of a pharmaceutical composition containing a compound selected from the group consisting of Formula (I) and Formula (II) or pharmaceutical composition thereof and an additional agent for treating or ameliorating a serine protease or dual-serine protease mediated disorder or the essentially simultaneous administration of a separate pharmaceutical composition containing a compound selected from the group consisting of Formula (I) and Formula (II) or pharmaceutical composition thereof and a separate pharmaceutical composition containing an additional agent for treating or ameliorating a serine protease or dual-serine protease mediated disorder.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

The ubiquitous nature of the Factor Xa and tryptase isoforms and their important roles in physiology provide incentive to produce highly selective Factor Xa and tryptase inhibitors. Given the evidence demonstrating linkage of certain isoforms to disease states, it is reasonable to assume that inhibitory compounds that are selective to a serine protease isoform or to a Factor Xa isoform relative to the a tryptase isoform and other serine proteases or dual-serine protease are superior therapeutic agents. Such compounds should demonstrate greater efficacy and lower toxicity by virtue of their specificity. Accordingly, it will be appreciated by one skilled in the art that a compound selected from the group consisting of Formula (I) and Formula (II) is therapeutically effective for certain serine protease or dual-serine protease mediated disorders based on the modulation of the disorder by selective serine protease or dual-serine protease inhibition. The usefulness of a compound selected from the group consisting of Formula (I) and Formula (II) as a selective serine protease or dual-serine protease inhibitor can be determined according to the methods disclosed herein and the scope of such use includes use in one or more serine protease or dual-serine protease mediated disorders.

More particularly, the term "serine protease or dual-serine protease mediated disorders" includes, and is not limited to, thrombotic disorders, arterial thrombosis, venous thrombosis, restenosis, hypertension, heart failure, arrhythmia, myocardial infarction, acute myocardial infarction, reocclusion following thrombolytic therapy, reocclusion following angioplasty, inflammation, angina, unstable angina, stroke, atherosclerosis, ischemic conditions, neurodegenerative disorders (associated with thrombotic or ischemic conditions), asthma and inflammatory bowel syndrome. Certain of the instant compounds are also useful as antithrombotics and anticoagulation agents in conjunction with fibrinolytic therapy (e.g., t-PA or streptokinase). The utility of the compounds to treat serine protease or dual-serine protease mediated disorders can be determined according to the procedures described herein.

Additionally, compounds of the present invention (such as Compound 27) may be useful in treating a chronic neurodegenerative disorder (such as Alzheimer's disease) (tested for activity using methodology similar to that described in Ermolieff, J., et al, Proteolytic Activation of Recombinant Pro-memapsin 2 (Pro-β-secretase) Studied with New Fluorogenic Substrates, *Biochemistry*, 2000, 39, 12450–12456).

The present invention further provides pharmaceutical compositions comprising one or more compounds of this invention in association with a pharmaceutically acceptable carrier.

As used herein, the term "composition" is intended to encompass a product comprising the specified ingredients in the specified amounts, as well as any product which results, directly or indirectly, from combinations of the specified ingredients in the specified amounts. Accordingly, pharmaceutical compositions containing the compounds of the present invention as the active ingredient as well as methods of preparing the instant compounds are also part of the present invention.

To prepare the pharmaceutical compositions of this invention, one or more compounds of Formula (I), Formula (II) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets*, Second Edition, Revised and Expanded, Volumes 1–3, edited by Lieberman, et al.; *Pharmaceutical Dosage Forms: Parenteral Medications*, Volumes 1–2, edited by Avis, et al.; and *Pharmaceutical Dosage Forms: Disperse Systems*, Volumes 1–2, edited by Lieberman, et al.; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg to about 300 mg (preferably, from about 0.1 mg to about 100 mg; and, more preferably, from about 1 mg to about 30 mg) and may be given at a dosage of from about 0.01 mg/kg/day to about 300 mg/kg/day (preferably, from about 0.1 mg/kg/day to about 100 mg/kg/day; and, more preferably, from about 1 mg/kg/day to about 30 mg/kg/day). Preferably, in the method for treating thrombotic disorders described in the present invention and using any of the compounds as defined herein, the dosage form will contain a pharmaceutically acceptable carrier containing between about 0.01 mg and 100 mg; and, more preferably, between about 5 mg and 50 mg of the compound; and, may be constituted into any form suitable for the mode of administration selected. The dosages, however, may be varied depending upon the requirement of the subjects, the severity of the condition being treated and the compound being employed. The use of either daily administration or post-periodic dosing may be employed.

Preferably these compositions are in unit dosage forms such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and glidants. Suitable diluents include, but are not limited to, starch (i.e. com, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent comstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethycellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable glidants include, but are not limited to, talc, cornstarch, silica (i.e. CAB-O-SIL™ silica available from Cabot, SYLOID™ silica available from W. R. Grace/ Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate such as cellulose acetate phthalate, polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quatemary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxyethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) of lactide (which includes lactic acid d-, I- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

Compounds of this invention may be administered in any of the foregoing compositions and dosage regimens or by means of those compositions and dosage regimens established in the art whenever treatment of serine protease or dual-serine protease mediated disorders is required for a subject in need thereof.

The daily dose of a pharmaceutical composition of the present invention may be varied over a wide range from about 0.7 mg to about 21,000 mg per 70 kilogram (kg) adult human per day; preferably in the range of from about 0.7 mg to about 7,000 mg per adult human per day; and, more preferably, in the range of from about 0.7 mg to about 2,100 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. A therapeutically effective amount of the drug is ordinarily supplied at a dosage level of from about 0.01 mg/kg to about 300 mg/kg of body weight per day. Preferably, the range is from about 0.1 mg/kg to about 100 mg/kg of body weight per day; and, most preferably, from about 1 mg/kg to about 30 mg/kg of body weight per day. Advantageously, compounds of the present invention may be administered in a single daily dose or the total daily dosage may be administered in divided doses of two, three or four times daily.

Optimal dosages to be administered may be readily determined by those skilled in the art, and will vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

In the examples and throughout this application, the following abbreviations have the meanings recited hereinafter:

| Boc | t-Butoxycarbonyl |
| Cpd or Cpmd | Compound |
| DCC | 1,3-Dicyclohexylcarbodiimide |
| DIPEA | Diisopropylethylamine |
| DMF | N,N-Dimethylformamide |
| EtOAc | Ethyl acetate |
| h | Hour |
| $KHSO_4$ | Potassium bisulfate |
| MeOH | Methanol |
| min | Minute |
| mL | Milliliter |
| $NaBH_4$ | Sodium borohydride |
| $Na_2SO_4$ | Sodium sulfate |

| | |
|---|---|
| NaHCO$_3$ | Sodium bicarbonate |
| rt | room temperature |
| TFA | Trifluoroacetic acid |

GENERAL SYNTHETIC EXAMPLES

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

The following scheme describes general synthetic methods whereby intermediate and target compounds of the present invention may be prepared. Additional representative compounds of the present invention can be synthesized using the intermediates prepared in accordance with the schemes and other materials, compounds and reagents known to those skilled in the art.

GENERAL SYNTHETIC EXAMPLES

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

The following scheme describes general synthetic methods whereby intermediate and target compounds of the present invention may be prepared. Additional representative compounds of the present invention can be synthesized using the intermediates prepared in accordance with the schemes and other materials, compounds and reagents known to those skilled in the art.

Scheme A illustrates a general synthetic route for compounds of Formula (I).

In a modification of a known procedure (*Syn. Comm.* 1992, 22(19) 2357), the 3-aminopyrrolidine Compound A1 was treated with an aldehyde in a solvent such as toluene and the mixture was heated at reflux with water removal by a Dean-Stark apparatus. The required pyrrolidine intermediate for preparing compounds wherein $R_2$ is oxo may be made according to PCT application WO 98/05336. The required intermediate for compounds wherein $R_1$ is H may be made by using a commercially available 3-buytyloxycarbonylamino pyrrolidine or other known analog. Upon cooling to rt, the solution was treated with a protecting group reagent such as di-tent-butyl dicarbonate. The intermediate imine was dissolved in an anhydrous solvent such as methanol and treated with a reducing agent such as NaBH$_4$ to afford an amine Compound A2. Treatment of Compound A2 with an acid chloride such as 4-nitrobenzoyl chloride in a solvent such as CH$_2$Cl$_2$ followed by solvent removal and treatment with TFA afforded Compound A3.

Sulfonylation of Compound A3 can be carried out by treating Compound A3 with a sulfonyl halide in a solvent such as CH$_2$Cl$_2$ in the presence of an amine base such as DIPEA to afford Compound A4.

Treatment of Compound A4 with a reducing agent such as SnCl$_2$ in the presence of a mineral acid such as HCl in an alcoholic solvent such as MeOH afforded Compound A5.

Guanylation of Compound A5 was carried out by treating Compound A5 with a guanylating agent such N,N'-bis-tert-butoxycarbonylthiourea in the presence of HgCl$_2$, an amine base such as triethylamine in a solvent such as DMF to afford Compound A6. Treatment of Compound A6 with trifluoroacetic acid yielded the target compound of Formula (I).

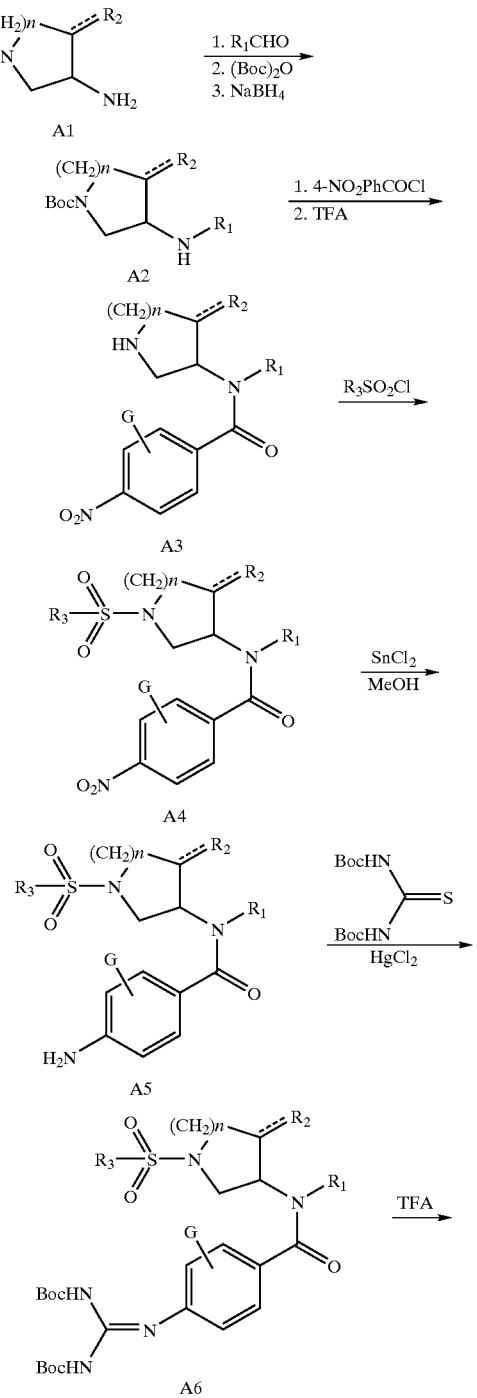

Scheme A

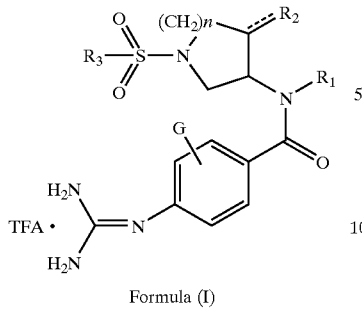

Formula (I)

Scheme B illustrates the general synthetic route for compounds of Formula (II).

The intermediate Compound A2 (Scheme A) was treated with a sulfonyl halide in a solvent such as $CH_2Cl_2$ in the presence of an amine base such as DIPEA to afford Compound B1. Treatment of Compound B1 with TFA in a solvent such as $CH_2Cl_2$ gave Compound B2. A mixture of Compound B2, an aromatic carboxylic acid chloride such as 4-nitrobenzoyl chloride and a base such as DIPEA in a solvent such as $CH_2Cl_2$ were stirred at rt to afford Compound B3.

Treatment of Compound B3 with a reducing agent such as $SnCl_2$ in the presence of a mineral acid such as HCl in an alcoholic solvent such as MeOH afforded Compound B4.

Guanylation of Compound B4 was carried out by treating Compound B4 with a guanylating agent such N,N'-bis-tert-butoxycarbonythiourea in the presence of $HgCl_2$ and an amine base such as triethylamine in a solvent such as DMF to afford Compound B5. Treatment of Compound B5 with trifluoroacetic acid in a solvent such as $CH_2Cl_2$ yielded the target compound of Formula (II).

Scheme B

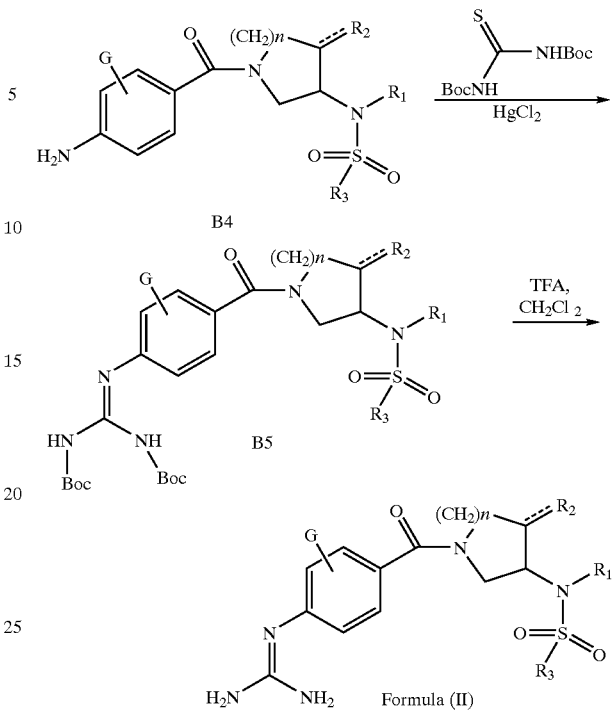

Formula (II)

SPECIFIC SYNTHETIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

All chemicals were obtained from commercial suppliers and used without further purification. $^1H$ and $^{13}C$ NMR spectra were recorded on a Bruker AC 300B (300 MHz proton) or a Bruker AM-400 (400 MHz proton) spectrometer with $Me_4Si$ as an internal standard (s=singlet, d=doublet, t=triplet, br=broad). APCl-MS and ES-MS were recorded on a VG Platform II mass spectrometer. TLC was performed with Whatman 250-μm silica gel plates. Preparative TLC was performed with Analtech 1000-μm silica gel GF plates. Flash column chromatography was conducted with flash column silica gel (40–63 μm) and column chromatography was conducted with standard silica gel. HPLC separations were carried out on three Waters PrepPak® Cartridges (25×100 mm, Bondapak® C18, 15–20 μm, 125 Å) connected in series; detection was at 254 nm on a Waters 486 UV detector. Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

Representative Chemical Abstracts Service (CAS) Index-like names for the compounds of the present invention were

Example 1

4-[[[1-[[(E)2-(4-Chlorophenyl)ethenyl]sulfonyl]-3-pyrrolidinyl][4-[(diaminomethylene)amino]benzoyl]amino]methyl]-benzoic Acid (Compound 5)

To a solution of Compound 1A (1.4 g, 16.0 mMol) in toluene (65 mL) was added methyl 4-formyl benzoate (2.6 g, 16.0 mMol). The reaction was refluxed (Dean-Stark trap) until water distillation ended (~30 min). The solution was cooled to rt and treated with di-tert-butyl dicarbonate (3.1 g, 16.0 mMol) in one portion. After stirring overnight, the reaction was concentrated to yield Compound 1B as a yellow-brown oil: $^1$H NMR (CDCl$_3$) δ 1.37–1.58 (m, 9H), 1.71–2.22 (overlapping m, 3H), 3.32–3.73 (overlapping m, 4H), 3.88–4.09 (overlapping m, 4H), 7.71 (d, 2H), 8.09 (d, 2H), 8.37 (s, 1H) ppm.

To a solution of Compound 1B at 0° C. in 50 mL of MeOH was added excess NaBH$_4$ (0.8 g, 21.1 mMol). The ice bath was removed and the solution was warmed to rt. To the solution was added 3 mL of acetone, and the solution was concentrated to yield a gummy solid which was partitioned between EtOAc and brine. The layers were separated and the aqueous layer was extracted with EtOAc. The combined extracts were filtered and dried over Na$_2$SO$_4$. The solution was filtered through Celite and concentrated to yield Compound 1C as an orange oil: 5.5 g; HPLC: 2.42 min, 100%; ES-MS 335(MH$^+$); $^1$H NMR (CDCl$_3$) δ 1.48 (s, 9H), 1.66–1.81 (m, 1H), 1.98–2.11 (m, 1H), 3.04–3.22 (m, 1H), 3.26–3.62 (overlapping m, 4H), 3.87 (s, 2H), 3.92 (s, 3H), 7.4 (d, 2H), 8.0 (d, 2H).

To a solution of Compound 1C (1.1 g, 3.4 mMol) in CH$_2$Cl$_2$ (30 mL) was added DIPEA (0.6 mL, 3.4 mMol) followed by p-nitrobenzoyl chloride (0.6 g, 3.4 mMol). After 40 min, the reaction was concentrated and the residue was treated with 25 mL of TFA and stirred for 25 min. The solution was concentrated to yield Compound 1D as an orange oil: HPLC 2.55 min, 91%; ES-MS 384 (MH$^+$).

To a solution of Compound 1D in CH$_2$Cl$_2$ (30 mL) was added DIPEA (6.5 mL, 37.3 mMol) followed by 0.9 g, 3.7 mMol) of p-chlorolstyrylsulfonyl chloride (prepared as in WO 96/10022) and stirred for 30 min. The reaction solution was washed sequentially with 2×1N KHSO$_4$, 2×sat. NaHCO$_3$, 1×brine, and filtered. The filtrate was dried over Na$_2$SO$_4$, filtered through Celite, and concentrated to yield Compound 1E as a brown foam: 2.0 g; HPLC 4.04 min, 85%.

To a suspension of Compound 1E (1.8 g, 3.1 mMol) in MeOH (40 mL) was added a solution of SnCl$_2$ (2.9 g, 15.4 mMol) in concentrated HCl (10 mL) and refluxed for 1.5 h. The solution was concentrated, made basic (blue litmus) 1N NaOH and extracted twice with EtOAc. The combined extracts were washed with brine, dried over Na$_2$SO$_4$, filtered and concentrated to yield 1.5 g of Compound 1F as a yellow glass.; HPLC 3.38 min, 81%.

To a solution of Compound 1F (1.6 g, 2.9 mMol) in DMF (30 mL) was added (1.2 g, 4.4 mMol) of N,N'-bis-tert-butoxycarbonylthiourea (*Syn. Comm.* 1993, 23(10), 1443.) followed by TEA (1.4 mL, 9.7 mMol). To the solution was added 1.2 g (4.4 mMol) of HgCl$_2$. After 5 h, the black reaction mixture was diluted with EtOAc (150 mL) and filtered through Celite. The resulting light orange solution was washed sequentially with water and brine, filtered, dried over Na$_2$SO$_4$ and concentrated. The residue was purified by flash column chromatography (silica gel, CH$_2$Cl$_2$:MeOH; 100%→99:1) to yield Compound 1G as a white solid: (0.9 g, 38.5%); HPLC 99% 4.48 min; ES-MS 796 (MH$^+$).

To a solution of Compound 1G (0.1 g, 0.1 mMol) in 1,4-dioxane (18 mL) was added a solution of LiOH.H$_2$O (16 mg, 0.4 mMol) in H$_2$O (2 mL) and stirred overnight. The reaction solution was concentrated, acidified with excess 1N KHSO$_4$, and extracted three times with EtOAc. The combined extracts were washed with brine, dried over Na$_2$SO$_4$, filtered and concentrated. The residue was purified by flash column chromatography (silica gel, 98:2 CH$_2$Cl$_2$:MeOH) to afford Compound 1H as a white powder: (48 mg, 51%); HPLC 4.25 min; 99%.

A solution of Compound 1H (48 mg, 0.06 mMol) was dissolved in 2 mL of TFA and stirred for 30 min. The solution was concentrated to yield a clear oil which was triturated 2×Et$_2$O and dried under vacuum at rt to yield Compound 5 as a white solid: (37.0 mg, 85%); HPLC 2.76 min, 100%. ES-MS 582 (MH$^+$); $^1$H NMR (DMSO-d$_6$) δ 5 1.88–2.12 (broad s, 2H), 2.92–3.53 (overlapping m, 4H), 4.38–4.58 (overlapping m, 3H), 7.07–7.98 (m, 18H), 9.98 (broad s, 1H).

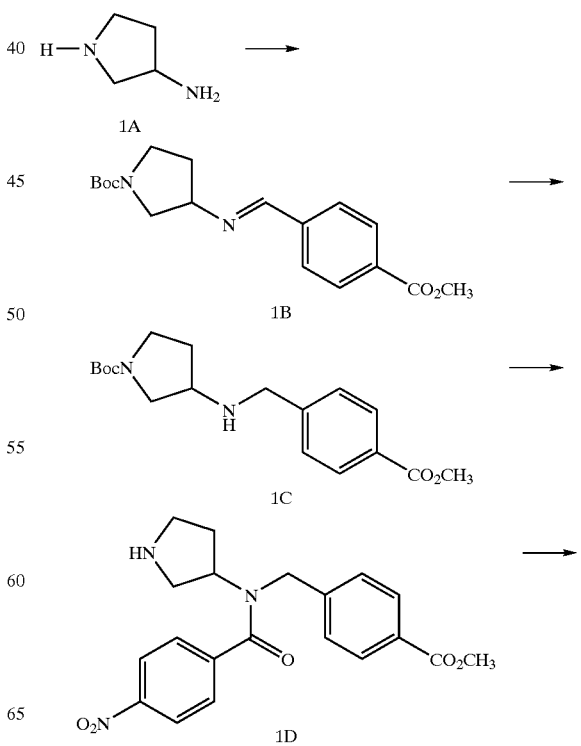

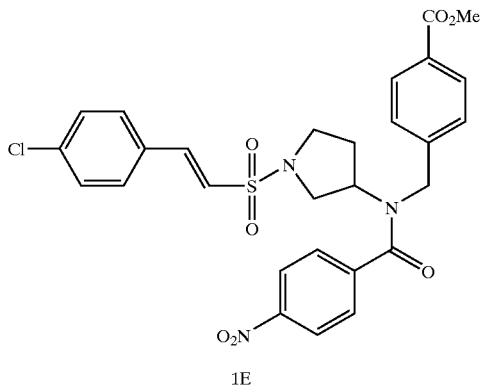

1E

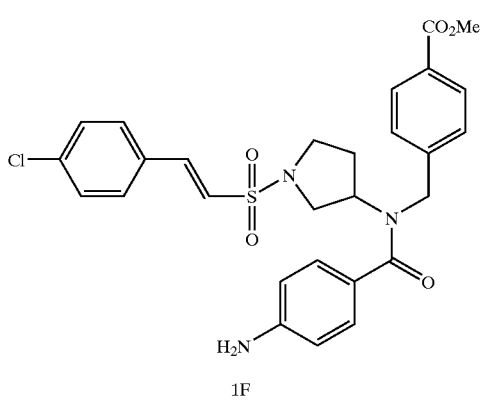

1F

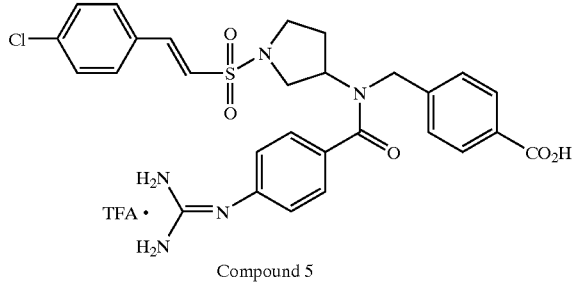

Compound 5

Using the procedure of Example 1 and the appropriate reagents and starting materials known to those skilled in the art, other compounds of the present invention may be prepared including, but not limited to:

| Cpd | Name | ES-MS m/z (MH+) |
|---|---|---|
| 1 | N-[1-[[(E)-2-(4-chlorophenyl)ethenyl]sulfonyl]-3-pyrrolidinyl]-4-[(diaminomethylene)amino]-N-(phenylmethyl)-benzamide | 538 |
| 2 | N-[1-[[(E)-2-(4-chlorophenyl)ethenyl]sulfonyl]-3-pyrrolidinyl]-4-[(diaminomethylene)amino]-N-[(4-hydroxyphenyl)methyl]-benzamide | 554 |
| 3 | 4-[[[1-[[(E)-2-(4-chlorophenyl)ethenyl]sulfonyl]-3-pyrrolidinyl][4-[(diaminomethylene)amino]benzoyl]amino]methyl]-benzoic acid methyl ester | 596 |
| 4 | 3-[[[1-[[(E)-2-(4-chlorophenyl)ethenyl]sulfonyl]-3-pyrrolidinyl][4-[(diaminomethylene)amino]benzoyl]amino]methyl]-benzoic acid methyl ester | 596 |
| 6 | 3-[[[1-[[(E)-2-(4-chlorophenyl)ethenyl]sulfonyl]-3-pyrrolidinyl][4-[(diaminomethylene)amino]benzoyl]amino]methyl]-benzoic acid | 582 |
| 7 | N-[1-[[(E)-2-(4-chlorophenyl)ethenyl]sulfonyl]-3-pyrrolidinyl]-4-[(diaminomethylene)amino]-N-[(3-hydroxyphenyl)methyl]-benzamide | 554 |
| 8 | [3-[[[1-[[(E)-2-(4-chlorophenyl)ethenyl]sulfonyl]-3-pyrrolidinyl][4-[(diaminomethylene)amino]benzoyl]amino]methyl]phenoxy]-acetic acid methyl ester | 626 |
| 9 | N-[[4-(aminocarbonyl)phenyl]methyl]-N-[1-[[(E)-2-(4-chlorophenyl)ethenyl]sulfonyl]-3-pyrrolidinyl]-4-[(diaminomethylene)amino]-benzamide | 581 |
| 10 | [[4-[[[1-[[(E)-2-(4-chlorophenyl)ethenyl]sulfonyl]-3-pyrrolidinyl][4-[(diaminomethylene)amino]benzoyl]amino]methyl]benzoyl]amino]-acetic acid methyl ester | 653 |
| 11 | [3-[[[1-[[(E)-2-(4-chlorophenyl)ethenyl]sulfonyl]-3-pyrrolidinyl][4-[(diaminomethylene)amino]benzoyl]amino]methyl]phenoxy]-acetic acid | 612 |
| 12 | [[4-[[[1-[[(E)-2-(4-chlorophenyl)ethenyl]sulfonyl]-3-pyrrolidinyl][4-[(diaminomethylene)amino]benzoyl]amino]methyl]benzoyl]amino]-acetic acid | 639 |
| 13 | [[3-[[[1-[[(E)-2-(4-chlorophenyl)ethenyl]sulfonyl]-3-pyrrolidinyl][4-[(diaminomethylene)amino]benzoyl]amino]methyl]benzoyl]amino]-acetic acid methyl ester | 653 |
| 14 | [[3-[[[1-[[(E)-2-(4-chlorophenyl)ethenyl]sulfonyl]-3-pyrrolidinyl][4-[(diaminomethylene)amino]benzoyl]amino]methyl]benzoyl]amino]-acetic acid | 639 |
| 15 | 3-[[[1-[[(E)-2-(4-chlorophenyl)ethenyl]sulfonyl]-3-pyrrolidinyl][4-[(diaminomethylene)amino]benzoyl]amino]methyl]-benzamide | 581 |

-continued

| Cpd | Name | ES-MS m/z (MH+) |
|---|---|---|
| 24 | N-[[4-[(aminoiminomethyl)amino]phenyl]methyl]-N-[1-[[(E)-2-(4-chlorophenyl)ethenyl]sulfonyl]-3-pyrrolidinyl]-4-[(diaminomethylene)amino]-benzamide | 595 |
| 25 | 5-[[[1-[[(E)-2-(4-chlorophenyl)ethenyl]sulfonyl]-3-pyrrolidinyl][4-[(diaminomethylene)amino]benzoyl]amino]methyl]-2-hydroxy-benzoic acid methyl ester | 612 |
| 26 | N-[1-[[(E)-2-(4-chlorophenyl)ethenyl]sulfonyl]-3-pyrrolidinyl]-4-[(diaminomethylene)amino]-benzamide | 448 |
| 27 | 4-[(aminoiminomethyl)amino]-N-(2-benzofuranyl-methyl)-N-[1-[[(E)-2-(4-chlorophenyl)ethenyl]sulfonyl]-3-pyrrolidinyl]-benzamide | 578 |

EXAMPLE 2

4-[[[[(E)-2-(4-Chlorophenyl)ethenyl]sulfonyl] [1-[4-[(Diaminomethylene)amino]benzoyl]-3-pyrrolidinyl] amino]methyl]-benzoic Acid (Compound 21)

To a solution of Compound 1C (prepared in Example 1; 0.90 g, 2.7 mMol) in $CH_2Cl_2$ (30 mL) was added DIPEA (0.5 mL, 2.7 mMol) followed by p-chlorostyrylsulfonyl chloridel (0.7 9, 2.7 mMol) and stirred at rt overnight. The reaction was cooled to rt and washed sequentially with 1N $KHSO_4$ and brine. The compound bined extracts were dried ($Na_2SO_4$), filtered and concentrated to afford Compound 2A as an orange foam: HPLC 4.31 min; 86%. Compound 2A was treated with 20 mL of TFA and stirred for 3.25 h. The solution was concentrated to afford Compound 2B as a brown oil: 2.3 g. To a solution of Compound 2B in $CH_2Cl_2$ (30 mL) was added DIPEA (2.0 mL, 11.5 mMol) followed by p-nitrobenzoyl chloride (0.4 g, 2.3 mMol) and stirred for 1 h. The solution was washed sequentially with 1N HCl, $H_2O$, 1N NaOH, and brine, then dried ($Na_2SO_4$), filtered and concentrated to yield Compound 2C: 1.5 g; HPLC: 4.0 min, 75%.

To a suspension of Compound 2C (1.5 g, 2.5 mMol) in MeOH (30 mL) was added $SnCl_2$ (2.4 g, 12.7 mMol) dissolved in conc. HCl (15 mL) and the resulting suspension heated to reflux. After 30 min at reflux, the reaction was cooled to rt, concentrated, and made basic with 1N NaOH. The mixture wasextracted twice with EtOAc, and the combined extracts were dried over $Na_2SO_4$, filtered and concentrated. The residue was purified by flash column chromatography (Biotage Flash 40 column, Isco UA-6 gradient pump; $CH_2Cl_2$:MeOH; 98:2→94:6) to yield Compound 2D as an off white solid: (0.4 g, 31%); HPLC 3.34 min, 100%; ES-MS 595 (MH+).

A solution of Compound 2D (0.4 g, 0.8 mMol) and N,N'-bis-tert-butoxycarbonylthiourea (Syn. Comm. 1993, 23(10), 1443; 0.3 g, 1.2 mMol) in 15 mL of DMF was treated with TEA (0.4 mL, 2.6 mMol) followed by $HgCl_2$ (1.8 mMol, 0.5 g) and the reaction was stirred overnight. The black suspension was diluted with EtOAc (150 mL) and filtered through Celite. The filtrate was washed sequentially with $H_2O$ and brine, filtered, dried ($Na_2SO_4$), and concentrated. The residue was purified by flash column chromatography (Biotage Flash 40 column, Isco UA-6 gradient pump; $CH_2Cl_2$:MeOH; 100%→96:4) to yield Compound 2E as a white solid: (0.5 g, 73%); HPLC 4.51 min, 100%.

To a solution of Compound 2E (0.4 g, 0.5 mMol) in 1,4-dioxane (18 mL) was added a solution of $LiOH.1H_2O$ (58 mg, 1.4 mMol) in $H_2O$ (2 mL) and stirred for 48 hr. The solution was concentrated, acidified with 1N $KHSO_4$, and extracted twice with EtOAc. The combined extracts were washed with brine, dried over $Na_2SO_4$, filtered through Celite and concentrated. The residue was purified by flash column chromatography (Biotage Flash 40 column, Isco UA-6 gradient pump; $CH_2Cl_2$:MeOH; 100%→94:6) to yield Compound 2F as a white powder: (0.2 g, 33%); HPLC: 4.31 min, 100%.

A solution of Compound 2F (63 mg, 0.08 mMol) in 2 mL of 100% TFA was stirred for 45 min. The solution was concentrated to yield a clear oil which was triturated twice with $Et_2O$ and dried under vacuum at rt to yield Compound 21 as a white solid: (43 mg, 77%); HPLC: 3.0 min 94%; ES-MS 582 (MH+); $^1$H NMR (DMSO-$d_6$) δ 1.75–2.13 (m, 2H), 3.12–3.79 (overlapping m, 4H), 4.31–4.68 (overlapping m, 3H), 7.08–8.11 (overlapping m, 18H), 10.0 (broad s, 1H).

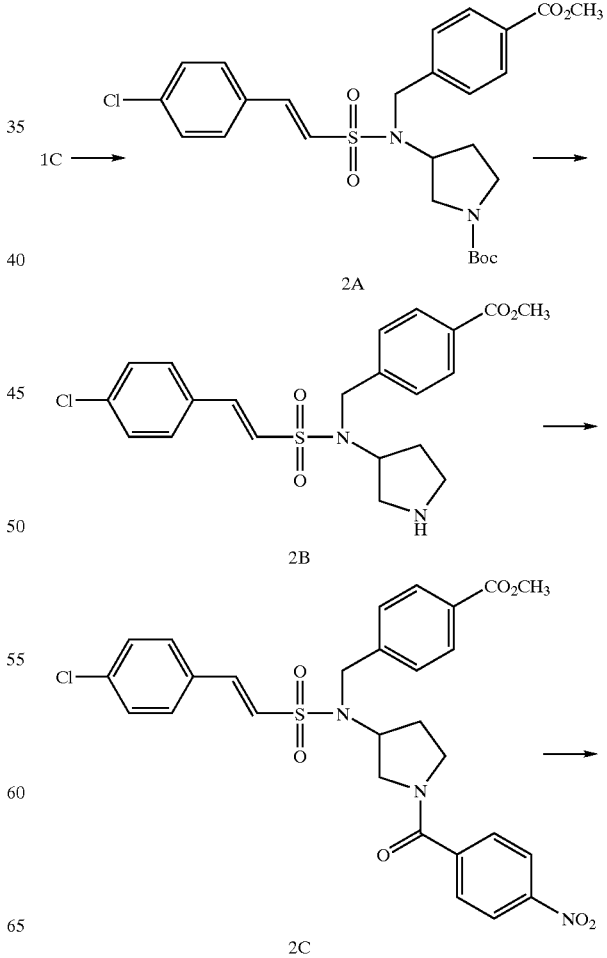

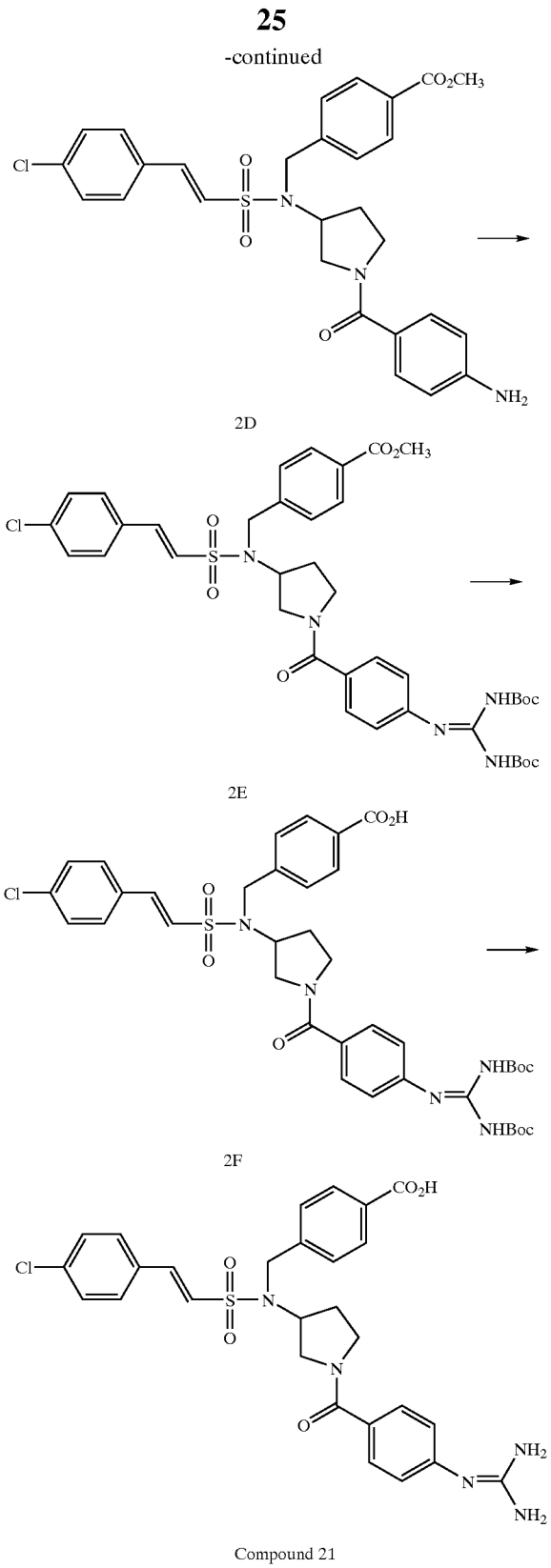

2D

2E

2F

Compound 21

Using the procedure of Example 2 and the appropriate reagents and starting materials known to those skilled in the art, other compounds of the present invention may be prepared including, but not limited to:

| Cpd | Name | ES-MS m/z (MH+) |
|---|---|---|
| 16 | 2-(4-chlorophenyl)-N-[1-[4-[(diaminomethylene)amino]benzoyl]-3-pyrrolidinyl]-N-(phenylmethyl)-(E)-ethenesulfonamide | 538 |
| 17 | 2-(4-chlorophenyl)-N-[1-[4-[(diaminomethylene)amino]benzoyl]-3-pyrrolidinyl]-N-[[4-(phenylmethoxy)phenyl]methyl]-(E)-ethenesulfonamide | 645 |
| 18 | 2-(4-chlorophenyl)-N-[1-[4-[(diaminomethylene)amino]benzoyl]-3-pyrrolidinyl]-N-[[4-(dimethylamino)phenyl]methyl]-(E)-ethenesulfonamide | 582 |
| 19 | 2-(4-chlorophenyl)-N-[1-[4-[(diaminomethylene)amino]benzoyl]-3-pyrrolidinyl]-N-[(4-methoxyphenyl)methyl]-(E)-ethenesulfonamide | 569 |
| 20 | 2-(4-chlorophenyl)-N-[1-[4-[(diaminomethylene)amino]benzoyl]-3-pyrrolidinyl]-N-(3-phenylpropyl)-(E)-ethenesulfonamide | 567 |
| 22 | 4-[[[[(E)-2-(4-chlorophenyl)ethenyl]sulfonyl][1-[4-[(diaminomethylene)amino]benzoyl]-3-pyrrolidinyl]amino]methyl]-benzoic acid methyl ester | 596 |
| 23 | N-[1-[4-[(diaminomethylene)amino]benzoyl]-3-pyrrolidinyl]-7-methoxy-N-(phenylmethyl)-2-naphthalenesulfonamide | 558 |

Biological Examples

The utility of the compounds of the present invention as serine protease or dual-serine protease inhibitors and, particularly, as Factor Xa or tryptase inhibitors useful as agents for the treatment of serine protease or dual-serine protease mediated disorders can be determined according to the procedures described herein.

Enzyme-Catalyzed Hydrolysis Assays

Factor Xa Inhibition

Enzyme-catalyzed hydolysis rates were measured spectrophotometrically using commercal human Factor Xa (American Diagnostica), the chromogenic sudstrate (MeO—CO—D—CHG—Gly-Arg-pNa (American Diagnostica); in aqueous buffer (50 mM Trisma Base, 0.1% Tween 80, pH 8.4), and a microplate reader (Molecular Devices). Changes in absorbance at 405 nM were monitored using the software program Softmax (Molecular Devices), upon addition of enzyme, with and without inhibitro present at 37° C. for 30 minutes. The $IC_{50}$ values were determined by fixing the enzyme and substrate concentrations (5.7 nM Factor Xa, 500 $\mu$M Factor Xa substrate) and varying the inhibitor concentration. Percent inhibition was calculated by comparing the initial reaction slopes of the without inhibitor samples to those with inhibitor. Inhibition constants ($K_i$) were detrmined by fixing the enzyme concentrations (5.7 nM Factor Xa) and inhibitor concentrations and varying the substrate concentrations (30–700 $\mu$M Factor Xa substrate. Michaelis-Menton kinetics were applied to the initial reaction slopes using the program Kcat (Bio Metallics Inc.).

Table 1 summarizes assay results for Factor Xa inhibition for certain compounds of the present invention:

TABLE 1

| Cpd | Factor Xa $K_i$ ($\mu$M) |
|---|---|
| 1 | 1.6 |
| 2 | 0.3 |
| 3 | 0.4 |
| 4 | 7.7 |
| 5 | 0.2 |
| 6 | 0.6 |
| 7 | 0.3 |
| 8 | 1.1 |
| 9 | 0.3 |
| 10 | 0.2 |
| 11 | 0.6 |
| 12 | 0.4 |
| 13 | 0.2 |
| 14 | 0.3 |
| 15 | 0.6 |
| 17 | 4.4 |
| 22 | 7.1 |
| 23 | 21 |
| 27 | 0.1 |

Tryptase Inhibition

The rate of increase in absorbance at 405 nM due to hydrolysis of synthetic chromogenic peptide substrates ([S]: 500 $\mu$M N-p-Tosyl-GLY-PRO-LYS-pNA; Sigma T-6140) is measured in the presence and absence of inhibitors (I) with a microplate reader at 37° C. The enzyme reaction is started by the addition of enzyme ([E]: 1.0 nM human Lung Tryptase; Cortex Biochem CP3033). Data is collected over a period of 30 min. and the initial rate of substrate hydrolysis (Vo (mOD/min)) is calculated. Inhibition is calculated by comparing to wells containing no inhibitor (vehicle) and $IC_{50}$s are determined using a four parameter fit logistics model.

Table 2 summarizes assay results for tryptase inhibition for certain compounds of the present invention:

TABLE 2

| Cpd | Tryptase $IC_{50}$ ($\mu$M) |
|---|---|
| 2 | 0.9 |
| 24 | 4.0 |
| 25 | 0.7 |
| 26 | 0.6 |

While the foregoing specification teaches the principles of the present invention, with examples provided for the purpose of illustration, it will be understood that the practice of the invention encompasses all of the usual variations, adaptaions and/or modifications as come within the scope of the following claims and their equivalents.

What is claimed is:

1. A compound selected from the group consisting of Formula (I)

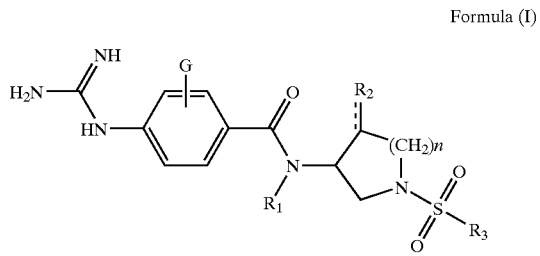

Formula (I)

wherein $R_1$ is selected from the group consisting of hydrogen, $C_{1-8}$alkyl, $C_{3-7}$cycloalkyl, aryl, aryl($C_{1-8}$)alkyl, aryl($C_{2-8}$)alkenyl, heteroaryl($C_{1-8}$)alkyl, heteroaryl($C_{2-8}$)alkenyl and $R_4C(O)CH_2$—; wherein aryl and heteroaryl are optionally substituted with one to two substituents independently selected from $R_4$;

$R_2$ is selected from the group consisting of hydrogen, hydroxy, $C_{1-8}$alkoxy, aryloxy and aryl($C_{1-8}$)alkoxy; with the proviso that $R_2$ is bonded to the heterocyclyl ring by a single bond; alternatively, $R_2$ is oxo; with the proviso that $R_2$ is bonded to the heterocyclyl ring by a double bond;

$R_3$ is selected from the group consisting of aryl, aryl($C_{1-8}$)alkyl, aryl($C_{2-8}$)alkenyl, heteroaryl($C_{1-8}$)alkyl, heteroaryl($C_{2-8}$)alkenyl; wherein aryl and heteroaryl are optionally substituted with one to three substituents independently selected from the group consisting of halogen, $C_{1-8}$alkyl, $C_{1-8}$alkoxy, amino, ($C_{1-4}$alkyl)amino, di($C_{1-4}$alkyl)amino, trihalo($C_{1-8}$)alkyl and trihalo($C_{1-8}$)alkoxy;

$R_4$ is selected from the group consisting of hydroxy, amino, $C_{1-8}$alkyl, ($C_{1-4}$alkyl)amino, di($C_{1-4}$alkyl)amino, $C_{1-8}$alkoxy, carboxy, carboxy($C_{1-8}$)alkyl, carboxy($C_{1-8}$)alkoxy, (carboxy)amino, (carboxy($C_{1-4}$)alkyl)amino, (carboxyaryl)amino, (carboxyaryl($C_{1-4}$)alkyl)amino, (carboxy($C_{1-4}$)alkylaryl)amino, aryloxy, aryl($C_{1-8}$)alkoxy, (aryl)amino, (aryl($C_{1-4}$)alkyl)amino, ($C_{1-4}$alkylaryl)amino, (arylcarboxy)amino, di(aryl)amino, di(aryl($C_{1-8}$)alkyl)amino, $C_{1-8}$alkoxycarbonyl, $C_{1-8}$alkoxycarbonyl($C_{1-8}$)alkoxy, aminocarbonyl, ($C_{1-8}$alkyl)aminocarbonyl, (carboxy($C_{1-8}$)alkyl) aminocarbonyl, ($C_{1-8}$alkoxycarbonyl($C_{1-8}$)alkyl) aminocarbonyl and guanidino; and, G is selected from the group consisting of hydrogen, halogen, hydroxy, $C_{1-4}$alkyl, $C_{1-8}$alkoxy, aryl, aryloxy, aryl($C_{1-8}$)alkyl, aryl($C_{1-8}$)alkoxy, amino, carboxy, alkylaminocarbonyl, alkylcarbonylamino, trihalo($C_{1-8}$)alkyl and trihalo($C_{1-8}$)alkoxy;

n is 2 and pharmaceutically acceptable salts thereof.

2. The compound of claim 1 wherein $R_1$ is selected from the group consisting of hydrogen, aryl($C_{1-8}$)alkyl and heteroaryl($C_{1-8}$)alkyl, wherein the aryl and heteroaryl portion of arylalkyl and heteroarylalkyl are optionally substituted with a substituent selected from $R_4$.

3. The compound of claim 1 wherein $R_1$ is selected from the group consisting of hydrogen, benzyl, phenethyl, phenylpropyl and benzofurylmethyl, wherein phenyl, the phenyl portion of benzyl and the benzofuryl portion of benzofurylmethyl are optionally substituted with a substituent selected from $R_4$.

4. The compound of claim 1 wherein $R_1$ is selected from the group consisting of hydrogen, benzyl, phenylpropyl and benzofurylmethyl, wherein phenyl, the phenyl portion of benzyl and the benzofuryl portion of benzofurylmethyl are optionally substituted with a substituent selected from $R_4$.

5. The compound of claim 1 wherein $R_2$ is hydrogen.

6. The compound of claim 1 wherein $R_3$ is aryl($C_{2-8}$) alkenyl, wherein aryl is optionally substituted with one to three substituents independently selected from halogen.

7. The compound of claim 1 wherein $R_3$ is a substituent independently selected from the group consisting of phenethenylene and phenylpropenylene, wherein phenyl is optionally substituted with one to three substituents independently selected from the group consisting of chlorine and fluorine.

8. The compound of claim 1 wherein $R_3$ is phenethenylene, wherein phenyl is substituted with one to three substituents selected from chlorine.

9. The compound of claim 1 wherein $R_4$ is selected from the group consisting of hydroxy, di($C_{1-4}$alkyl)amino, $C_{1-8}$alkoxy, carboxy, carboxy($C_{1-8}$)alkoxy, aryl($C_{1-8}$)alkoxy, $C_{1-8}$alkoxycarbonyl, $C_{1-8}$alkoxycarbonyl($C_{1-8}$)alkoxy, aminocarbonyl, ($C_{1-8}$alkyl)aminocarbonyl, (carboxy($C_{1-8}$)alkyl)aminocarbonyl and $C_{1-8}$alkoxycarbonyl($C_{1-8}$)alkyl)aminocarbonyl.

10. The compound of claim 1 wherein $R_4$ is selected from the group consisting of hydroxy, carboxy, carboxy($C_{1-8}$)alkoxy, $C_{1-8}$alkoxycarbonyl, $C_{1-8}$alkoxycarbonyl($C_{1-8}$)alkoxy, aminocarbonyl, (carboxy($C_{1-8}$)alkyl)aminocarbonyl and $C_{1-8}$alkoxycarbonyl($C_{1-8}$)alkyl)aminocarbonyl.

11. The compound of claim 1 wherein $R_4$ is selected from the group consisting of hydroxy, carboxy, carboxymethoxy, methoxycarbonyl, aminocarbonyl, (carboxymethylene) aminocarbonyl and methoxycarbonylmethylene) aminocarbonyl.

12. The compound of claim 1 wherein G is selected from the group consisting of hydrogen, halogen, hydroxy, $C_{1-4}$alkyl, $C_{1-8}$alkoxy, aryl, aryloxy, aryl($C_{1-8}$)alkyl, aryl ($C_{1-8}$)alkoxy, amino and trihalo($C_{1-8}$)alkyl.

13. The compound of claim 1 wherein G is hydrogen.

14. A pharmaceutical composition comprising a compound of claim 1 and a pharmaceutically acceptable carrier.

15. A pharmaceutical composition made by mixing a compound of claim 1 and a pharmaceutically acceptable carrier.

16. A process for preparing a pharmaceutical composition comprising mixing a compound of claim 1 and a pharmaceutically acceptable carrier.

17. A method for treating a serine protease or dual-serine protease mediated disorder in a subject in need thereof comprising administering to the subject a therapeutically effective amount of a compound of claim 1.

18. The method of claim 17 wherein the disorder is mediated by selective inhibition of a serine protease.

19. The method of claim 18 wherein the serine protease is selected from the group consisting of Factor Xa and tryptase.

20. The method of claim 17 wherein the disorder is mediated by dual inhibition of at least two serine proteases.

21. The method of claim 20 wherein the serine protease is selected from the group consisting of at least Factor Xa and tryptase.

22. The method of claim 17 wherein the serine protease or dual-serine protease mediated disorder is selected from the group consisting of thrombotic disorders, arterial thrombosis, venous thrombosis, restenosis, hypertension, heart failure, arrhythmia, myocardial infarction, acute myocardial infarction, reocclusion following thrombolytic therapy, reocclusion following angioplasty, inflammation, angina, unstable angina, stroke, atherosclerosis, ischemic conditions, neurodegenerative disorders (associated with thrombotic or ischemic conditions), asthma and inflammatory bowel syndrome.

23. The method of claim 17 wherein the therapeutically effective amount of the compound of claim 1 is from about 0.001 mg/kg/day to about 300 mg/kg/day.

* * * * *